United States Patent

Böhm et al.

Patent Number: 5,434,303
Date of Patent: Jul. 18, 1995

[54] PROCESS FOR THE PREPARATION OF 1-FLUORO-CYCLOPROPANE-1-CARBOXYLIC ACID

[75] Inventors: Stefan Böhm; Albrecht Marhold, both of Leverkusen, Germany

[73] Assignee: Bayer Aktiengesellschaft, Leverkusen, Germany

[21] Appl. No.: 158,080

[22] Filed: Nov. 24, 1993

Related U.S. Application Data

[63] Continuation of Ser. No. 942,564, Sep. 9, 1992, abandoned.

[30] Foreign Application Priority Data

Sep. 19, 1991 [DE] Germany ............... 41 31 139.6

[51] Int. Cl.⁶ ............................................. C07C 61/04
[52] U.S. Cl. .................................. 562/506; 560/124
[58] Field of Search ................................. 562/506

[56] References Cited

U.S. PATENT DOCUMENTS 4,913,727  4/1990  Stroech et al. .
5,089,640  2/1992  Böckmann et al. .

FOREIGN PATENT DOCUMENTS 0436348  7/1991  European Pat. Off. .

OTHER PUBLICATIONS

House, "Modern Synthetic Reaction," 2nd Ed pp. 321–329 (1972).
Roberts, "Basic Principles of Organic Chemistry," pp. 555–561.

*Primary Examiner*—Michael L. Shippen
*Attorney, Agent, or Firm*—Sprung Horn Kramer & Woods

[57] ABSTRACT

A new process for the preparation of 1-fluoro-cyclopropane-1-carboxylic acid of the formula

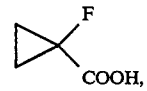

which process comprises
a) reacting in a first step, a 1-fluoro-cyclopropyl phenyl ketone of the formula

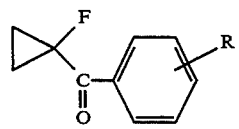

in which
R represents hydrogen, halogen, methyl, methoxy, phenyl or phenoxy,
with an peroxy compound in the presence of a diluent, and
b) reacting, in a second step, the resulting 1-fluoro-cyclopropane-1-carboxylate of the formula

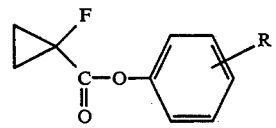

in which
R has the abovementioned meaning,
with a base in the presence of a diluent, and then acidifying the mixture.

New 1-fluoro-cyclopropane-1-carboxylates of the above-mentioned formula.

7 Claims, No Drawings

PROCESS FOR THE PREPARATION OF 1-FLUORO-CYCLOPROPANE-1-CARBOXYLIC ACID

This application is a continuation of application Ser. No. 942,564, filed Sep. 9, 1992, now abandoned.

The present invention relates to a new process for the preparation 1-fluoro-cyclopropane-1-carboxylic acid, which is known and which can be used as intermediate for the synthesis of active compounds which have fungicidal properties.

It has already been disclosed that 1-fluoro-cyclopropane-1-carboxylic acid can be prepared by oxidation of 1-fluoro-cyclopropyl methyl ketone (cf. EP-OS [European Published Specification] 0,436,348). However, the disadvantage of this process is that the compound required as starting material is only accessible by a multi-step synthesis, and the yields in the individual reaction steps are only relatively poor.

It has now been found that 1-fluoro-cyclopropane-1-carboxylic acid, of the formula $$\triangleright\!\!\!<^{F}_{COOH} \quad (I)$$

is obtained when a) in a first step, 1-fluoro-cyclopropyl phenyl ketones of the formula $$\triangleright\!\!\!<^{F}_{\underset{O}{\overset{\|}{C}}-\!\!\!\!\diagup\!\!\!\!\diagdown\!-R} \quad (II)$$

in which

R represents hydrogen, halogen, methyl, methoxy, phenyl or phenoxy, are reacted with peroxy compounds in the presence of a diluent and b) in a second step, the resulting 1-fluoro-cyclopropane-1-carboxylates of the formula $$\triangleright\!\!\!<^{F}_{\underset{O}{\overset{\|}{C}}-O-\!\!\!\!\diagup\!\!\!\!\diagdown\!-R} \quad (III)$$

in which

R has the abovementioned meaning, are reacted with bases in the presence of a diluent, and the reaction mixture is then acidified.

It must be regarded as extremely surprising that 1-fluoro-cyclopropane-1-carboxylic acid can be prepared by the process according to the invention in a smooth reaction with a high yield. This is because, taking into account the known prior art, it was to be expected that during the treatment with peroxy compounds not the phenyl ring but the cyclopropyl radical would migrate during the rearrangement reaction, giving cyclopropyl esters instead of phenyl esters. It is also unexpected that the fluorinated cyclopropyl radical is attacked to only a negligible degree during the reaction.

The process according to the invention is distinguished by a series of advantages. For example, it allows 1-fluoro-cyclopropane-1-carboxylic acid to be prepared in very good yields and high purity. Furthermore, the starting substances required are accessible in a simple manner and in larger amounts.

If 1-fluoro-cyclopropyl 4-chloro-phenyl ketone is used as starting substance, m-chloroperbenzoic acid as peroxy compound, sodium hydroxide as base and hydrochloric acid as acidifying agent, the course of the process according to the invention can be illustrated by the following equation:

[reaction scheme]

Formula (II) provides a general definition of the 1-fluoro-cyclopropyl phenyl ketones required as starting substances when carrying out the process according to the invention. In this formula, R preferably represents hydrogen, fluorine, chlorine, bromine, methyl, methoxy, phenyl or phenoxy.

Particularly preferred compounds of the formula (II) are those in which

R represents hydrogen or

R is bonded in the 4-position and represents fluorine, chlorine, bromine, methyl, methoxy, phenyl or phenoxy.

The 1-fluoro-cyclopropyl phenyl ketones of the formula (II) are known or can be prepared in a simple manner by processes known in principle (of. EP-OS [European Published Specification] 0,180,136).

Peroxy compounds which are suitable for carrying out the first step of the process according to the invention are all organic and inorganic substances which have a peroxide group and which are customary for reactions of this type. The following can preferably be used: peracids such as perbenzoic acid, m-chloro-perbenzoic acid, peracetic acid, perpropionic acid and peroxy-trifluoroacetic acid, furthermore boron trifluoride/hydrogen peroxide and potassium peroxydisulphate in a mixture with sulphuric acid.

The peroxy compounds which are suitable are known.

The 1-fluoro-cyclopropane-1-carboxylates of the formula (III), which are obtained when the first step of the process according to the invention is carried out, are new.

Bases which are suitable for carrying out the second step of the process according to the invention are all inorganic hydroxy compounds customary for hydrolyses of this type. The following can preferably be used: alkali metal hydroxides such as sodium hydroxide and potassium hydroxide, and also alkaline earth metal hydroxides such as calcium hydroxide.

Acids which can be used for the acidification when the second step of the process according to the invention is carried out are all organic and inorganic acids which are customary for reactions of this type. Hydrochloric acid can preferably be used.

Suitable diluents for carrying out the first step of the process according to the invention are, preferably, halogenated aliphatic hydrocarbons, optionally halogenated aromatic hydrocarbons, and also aliphatic carboxylic acids. The following may be mentioned by way of example: methylene chloride, dichloroethane, chloroform, carbon tetrachloride, benzene, toluene, chlorobenzene, acetic acid and propionic acid.

When carrying out the first step of the process according to the invention, the reaction temperatures can be varied within a certain range. In general, the process is carried out at temperatures between −10° C. and 120° C., preferably between 0° C. and 100° C.

The first step of the process according to the invention is generally carried out under atmospheric pressure. However, it is also possible to carry out the process under increased or reduced pressure.

When carrying out the first step of the process according to the invention, 1 to 3 moles, preferably 1.2 to 2.5 moles, of peroxy compound are generally employed per mole of 1-fluoro-cyclopropyl phenyl ketone of the formula (II). Working-up is carried out by customary methods. In general, a procedure is followed in which the solid residue is filtered off with suction, if appropriate after having been cooled first, and the organic phase is washed in succession with aqueous sodium sulphite solution, with dilute aqueous sodium hydroxide solution and aqueous sodium chloride solution and then dried and concentrated.

Diluents which are suitable for carrying out the second step of the process according to the invention are, preferably, mixtures of water and ethers. Ethers which can preferably be used for this purpose are diethyl ether, methyl tert.-butyl ether, tetrahydrofuran and dioxane.

When carrying out the second step of the process according to the invention, the reaction temperatures can also be varied within a certain range. In general, the process is carried out at temperatures between −5° C. and +100° C., preferably between 0° C. and 60° C.

The second step of the process according to the invention is also generally carried out under atmospheric pressure. However, it is also possible to carry out the process under increased or reduced pressure.

When carrying out the second step of the process according to the invention, an equimolar amount of base is generally employed per mole of 1-fluoro-cyclopropane-1-carboxylate of the formula (III). However, it is also possible to employ only catalytic amounts, or an excess of the equimolar amount, of the base. In a specific variant, the ester cleavage can also be carried out with the aid of acids. Again, working-up is carried out by customary methods. In general, a procedure is followed in which the reaction mixture is extracted with an organic solvent which is sparingly soluble in water, the aqueous phase is acidified, if appropriate with cooling, the resulting mixture is extracted with an organic solvent which is sparingly soluble in water, and this organic phase is finally dried and concentrated. If appropriate, the resulting product can be freed from any contaminations which may be present by customary methods.

1-Fluoro-cyclopropane-1-carboxylic acid, of the formula (I), is a valuable intermediate for the synthesis of active compounds which have fungicidal properties (cf. EP-OS [European Published Specification] 0,436,348 and EP-OS [European Published Specification] 0,297,345). For example, the compound of the formula

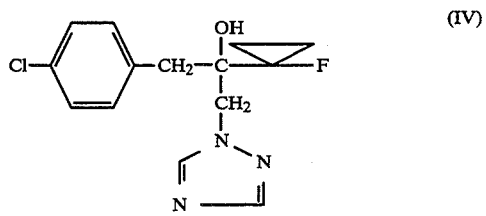

can be prepared by converting 1-fluoro-cyclopropane-1-carboxylic acid, of the formula

with the aid of thionyl chloride into the acid chloride, of the formula

then reacting the latter with 4-chlorobenzyl-zinc chloride, of the formula

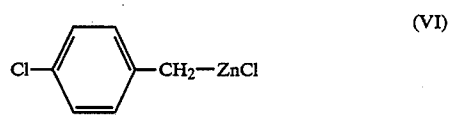

reacting the resulting ketone of the formula

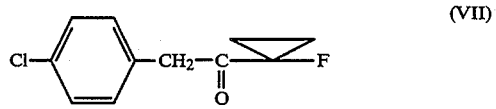

with dimethylsulphonium methylide, of the formula

and reacting the oxirane formed in this reaction, of the formula

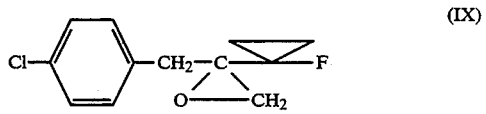

with 1,2,4-triazole.

The examples which follow illustrate how the process according to the invention is carried out.

EXAMPLE 1 a) Preparation of 4-chlorophenyl 1-fluoro-cyclopropane-1-carboxylate, of the formula

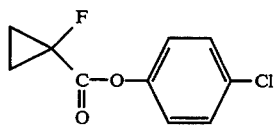

A solution of 130 g (0.65 mol) of 1-fluoro-cyclopropyl 4-chlorophenyl ketone in 1300 ml of chloroform is treated at room temperature with 225 g (0.9 mol) of m-chloroperbenzoic acid (70% strength). The mixture is stirred for 24 hours under reflux conditions. A further 120 g (0.48 mol) of m-chloroperbenzoic acid (70% strength) are then added, and the mixture is again stirred for 24 hours under reflux conditions. The reaction mixture is subsequently cooled with ice, and the precipitate which has formed is filtered off with suction and washed repeatedly with chloroform. The combined organic solutions are washed in succession with 10% strength aqueous sodium sulphite solution, twice with 5% strength aqueous sodium hydroxide solution and with dilute aqueous sodium chloride solution. The organic phase is dried over magnesium sulphate and then concentrated by stripping off the solvent under reduced pressure. In this manner, 104 g (75% of theory) of 4-chlorophenyl 1-fluoro-cyclopropane-1-carboxylate are obtained in the form of an oil.

$^{19}$F NMR (188 MHz, CDCl$_3$/CFCl$_3$): δ=198.2 ppm
$^1$H NMR (200 MHz, CDCl$_3$/TMS): δ=1.48–1.62 ppm (m, 4H, cyclopropyl-H), 7.08 and 7.34 ppm (AA'BB' system 4 H, arom. H).

b) Preparation of 1-fluoro-cyclopropane-1-carboxylic acid, of the formula

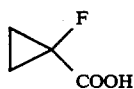

A solution of 138 g (0.64 mol) of 4-chlorophenyl 1-fluoro-cyclopropane-1-carboxylate in 250 ml of methyl tert.-butyl ether is treated at 0° C. with a solution of 25.6 g (0.64 mol) of sodium hydroxide in 250 ml of water. The mixture is stirred for 3 hours at room temperature and subsequently extracted for 18 hours in a liquid-liquid extractor, using methyl tert.-butyl ether. The aqueous phase is acidified with 150 ml of concentrated hydrochloric acid, with ice-cooling, and then extracted three times with 300 ml portions of diethyl ether. This organic phase is dried over magnesium sulphate and then concentrated by stripping off the solvent under reduced pressure. In this manner, 52 g (78% of theory) of 1-fluoro-cyclopropane-1-carboxylic acid are obtained in the form of a solid substance of melting point 66°–68° C.

$^{19}$F NMR (188 MHz, CDCl$_3$;CFCl$_3$): δ=199 ppm $^1$H NMR (200 MHz, CDCl$_3$/TMS): δ=1.40–1.52 ppm (m, 4H, cyclopropyl H), 9.25 ppm (1H, COOH).

c) Preparation of 1-fluoro-cyclopropyl 4-chlorophenyl ketone, of the formula

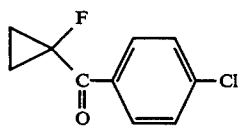

which is required as starting material.

2000 g (34.5 mol) of potassium fluoride are introduced into 7 liters of diethylene glycol, and the mixture is treated with 500 ml of toluene at room temperature. The toluene is distilled off at 150° C., and the mixture is then allowed to cool to 100° C., and 1500 g (5 mol) of 4-chloro-phenyl 1-bromo-3-chloro-n-propyl ketone are added in portions in the course of 15 minutes. The reaction mixture is heated for 4 hours at 150° C. and then cooled and poured into 10 liters of water. The resulting mixture is extracted five times with 2 liters of toluene per extraction, and the combined organic phases are washed with water, dried over magnesium sulphate and concentrated by stripping off the solvent under reduced pressure. The residue which remains is distilled under a high vacuum, and the distillate collected is subjected to fractional distillation under a high vacuum, using a spinning band column. In this manner, 100 g (10% of theory) of 1-fluorocyclopropyl 4-chlorophenyl ketone are obtained in the form of a liquid of boiling point 70°–76° C. at 0.03 mbar.

$^{19}$F NMR (188 MHz, CDCl$_3$/CFCl$_3$): δ=191.7 ppm
$^1$H NMR (200 MHz, CDCl$_3$/TMS): δ=1.39–1.62 ppm (m, 4H, cyclopropyl-H), 7.44 and 7.96 ppm (AA'BB' system, 4H arom. H).

Use Example

Preparation of the compound of the formula

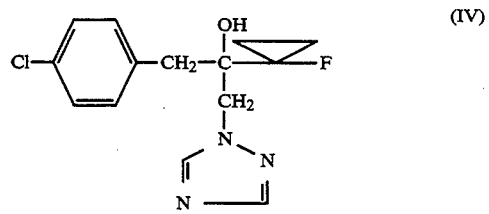

a) Preparation of the compound of the formula

3 drops of dimethylformamide and 71 g (0.6 mol) of thionyl chloride are introduced into 52 g (0.5 mol) of 1-fluoro-cyclopropane-1-carboxylic acid at room temperature. The mixture is slowly heated to reflux temperature whilst stirring and is subsequently stirred for 2 hours at this temperature. The mixture is then subjected to a fractional distillation. In this manner, 42.8 g (70% of theory) of 1-fluoro-cyclopropane-1-carboxylic acid chloride are obtained in the form of a liquid of boiling point 71° C. at 300 mbar.

$^{19}$F-NMR (188 MHz, CDCl$_3$/CFCl$_3$): δ=187, 4 ppm.
$^1$H-NMR (200 MHz, CDCl$_3$/TMS): δ=1,58–1,73 ppm (m, cyclopropyl-H)

b) Preparation of the compound of the formula

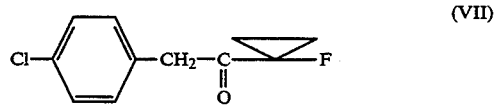

0.018 g of bis-(triphenylphosphine)-palladium (II) chloride and 6.1 (50 mmol) of 1-fluoro-cyclopropanecarboxylic acid chloride are introduced into a solution of 12.5 g (55 mmol) of 4-chlorobenzyl-zinc chloride in 60 ml of absolute dimethoxyethane at room temperature whilst stirring. The mixture is heated under reflux and under nitrogen atmosphere for 30 minutes whilst stirring. The reaction mixture is then treated with toluene and diluted, aqueous hydrochloric acid. The organic phase is separated off, washed twice with water dried over sodium sulphate and then concentrated by stripping off the solvent under reduced pressure. The remaining residue is heated briefly under a pressure of 0.05 mbar and under distillation conditions, the bath temperature being 70° C. In this manner 9.6 g of a yellowish solid substance are obtained, which according to gas chromatographical analysis consists of 70% of 4-chlorobenzyl-1-fluoro-cyclopropyl-ketone. Accordingly, the yield is calculated as 63% of theory. After recrystallization from a mixture of hexane and ethanol, there are obtained 3.3 g of 4-chlorobenzyl-1-fluoro-cyclopropyl ketone in the form of a yellowish solid substance of melting point 53°–54° C.

c) Preparation of the compound of the formula

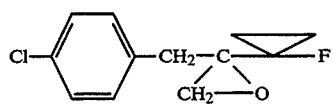
(IX)

In the course of 30 minutes, 21 ml of 45% strength by weight aqueous sodium hydroxide solution are added dropwise to a mixture of 2.2 g (17.1 mmol) of trimethyl-sulphoxomium chloride and 3.3 g (15.5 mmol) of 4-chlorobenzyl-(1-fluorocyclopropyl) ketone in 20 ml of toluene, while stirring at room temperature. When the addition has ended the reaction mixture is stirred for a further 2 hours at a temperature of 40° C. Subsequently, the phases are separated, and the aqueous phase is extracted three times with toluene. The combined organic phases are washed once with water, dried over sodium sulphate and concentrated under reduced pressure. The residue is used for the further reaction with additional purification.

d) Preparation of the compound of the formula

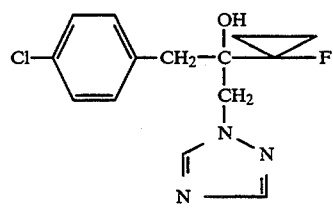
(IV)

A solution of 3.3 g (15.7 mmol) of 2-(4-chlorobenzyl)-2-(1-fluorocyclopropyl)-oxirane in 10 ml of dimethyl-formamide is added dropwise to a mixture of 3.3 g (47.1 mmol) of 1,2,4-triazole end 0.35 g (3.14 mmol) of potassium tert.-butylate in 20 ml of dimethylformamide at a temperature of 80° C., while stirring. When the addition has ended, the reaction mixture is stirred for 13 hours at 80° C. The solvent is then stripped off under reduced pressure, and the remaining residue is taken up with water. The aqueous phase is extracted four times with methylene chloride. The combined organic phases are dried over sodium sulphate and then concentrated under reduced pressure. The remaining residue is chromatographed over silica over silica gel using cyclohxane:ethylacetate=2:1 as the mobile phase. Evaporation of the eluate gives 2.2 g (47% of theory) of 1-(4-chlorophenyl)-2-(1-fluorocyclopropyl)-3-(1,2,4-triazol-1-yl)-propan-2-ol in form of a solid substance.

$^1$H-NMR (200 MHz, CDCl$_3$): δ=0.0–0.8 (m, 4H); 3.0 (AB-system, 2H); 4.01 (s,1H, OH); 4.3 (AB-system, 2H); 7.28 (s,4H); 7.98 (s, 1H); 8, 13 (s, 1H).

It will be understood that the specification and examples are illustrative but not limitative of the present invention and that other embodiments within the spirit and scope of the invention will suggest themselves to those skilled in the art.

What is claimed is:

1. A process for the preparation of 1-fluoro-cyclopropane-1-carboxylic acid of the formula

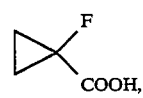

which process comprises a) reacting, in a first step, the 1-fluoro-cyclopropyl ketone of the formula

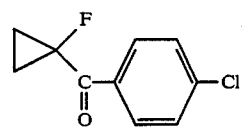

with a peroxy compound in the presence of a diluent, and b) reacting, in a second step, the resulting 1-fluoro-cyclopropane-1-carboxylate of the formula

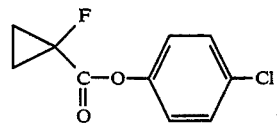

with a base in the presence of a diluent, and acidifying the reaction mixture.

2. A process as claimed in claim 1, wherein the peroxy compound is a compound selected from the group comprising perbenzoic acid, m-chloro-perbenzoic acid, peracetic acid, perpropionic acid, peroxy-trifluoroacetic acid, boron trifluoride/hydrogen peroxide and a mixture of potassium peroxydisulphate and sulphuric acid.

3. A process as claimed in claim 1, wherein the base is a compound selected from an alkaline earth metal hydroxide and an alkali metal hydroxide.

4. A process as claimed in claim 1, wherein the first step is carried out in the presence of a diluent selected from a halogenated aliphatic hydrocarbon, an optionally halogenated aromatic hydrocarbon and an aliphatic carboxylic acid.

5. A process as claimed in claim 1, wherein the diluent for carrying out the second step is a mixture of water and an ether.

6. A process as claimed in claim 1, wherein the first step is carried out at a temperature between −10° C. and +120° C.

7. A process as claimed in claim 1, wherein the second step is carried out at a temperature between −5° C. and +100° C.

* * * * *